US005734056A

United States Patent [19]
Burk et al.

[11] Patent Number: 5,734,056
[45] Date of Patent: Mar. 31, 1998

[54] PROCESS FOR THE PREPARATION OF CERTAIN 9-SUBSTITUTED CAMPTOTHECINS

[75] Inventors: Patrick Lee Burk, Freehold, N.J.; Joseph Marian Fortunak, Exton, Pa.; Antonietta Rose Mastrocola, Bala Cynwyd, Pa.; Mark Mellinger, Telford, Pa.; Jeffrey Lee Wood, Blue Bell, Pa.

[73] Assignee: SmithKline Beecham Corporation, Philadelphia, Pa.

[21] Appl. No.: 451,079

[22] Filed: May 25, 1995

Related U.S. Application Data

[63] Continuation of Ser. No. 418,914, Apr. 7, 1995, abandoned, which is a continuation of Ser. No. 87,147, Jul. 2, 1993, abandoned, which is a continuation of Ser. No. 946,251, Sep. 16, 1992, abandoned, which is a continuation of Ser. No. 589,643, Sep. 28, 1990, abandoned.

[51] Int. Cl.$^6$ ............................................. C07D 491/12
[52] U.S. Cl. .................... 546/48; 514/233.2; 514/253; 514/283; 544/125; 544/361
[58] Field of Search .................... 546/42, 48, 41; 544/125, 361

[56] References Cited

U.S. PATENT DOCUMENTS

| | | | |
|---|---|---|---|
| 4,473,692 | 9/1984 | Miyasaka et al. | 546/48 |
| 4,894,456 | 1/1990 | Wall et al. | 546/41 |
| 4,943,579 | 7/1990 | Vishnuvajjala et al. | 514/283 |
| 4,981,968 | 1/1991 | Wall et al. | 544/361 |
| 5,004,758 | 4/1991 | Boehm et al. | 514/283 |
| 5,061,800 | 10/1991 | Yaegashi et al. | 546/48 |
| 5,336,781 | 8/1994 | Giles | 548/486 |
| 5,352,789 | 10/1994 | Hinz | 546/48 |

FOREIGN PATENT DOCUMENTS

| | | | |
|---|---|---|---|
| 0321122 | 6/1989 | European Pat. Off. | 546/48 |
| 0325247 | 7/1989 | European Pat. Off. | 546/48 |
| 0005188 | 1/1984 | Japan | 546/48 |
| 0046284 | 3/1984 | Japan | 546/48 |

OTHER PUBLICATIONS

Wall, et al., J. Am. Chem. Soc., vol. 88(16), pp. 3888–3890 (1966).
Govindachari, et al., Indian J. Chem., vol. 10 (4), pp. 453–454 (1972).
Wani, et al., J. Med. Chem., vol. 29 (11), pp. 2358–2363 (1986).
Wani, et al., J. Med, Chem., vol. 30(10), pp. 1774–1779 (1987).
Gunasekera et al Jour. Nat. Prod. vol. 42 pp. 475–477 (1979).

*Primary Examiner*—Donald G. Daus
*Attorney, Agent, or Firm*—Yuriy P. Stercho; Stephen A. Venetianer; Edward T. Lentz

[57] ABSTRACT

A process for the preparation of water soluble camptothecin analogs, including methods for the preparation of intermediates thereof, and the compounds prepared by said process. Water soluble camptothecin analogs are prepared which may be used for inhibiting the growth of tumor cells sensitive to such analogs.

42 Claims, No Drawings

PROCESS FOR THE PREPARATION OF CERTAIN 9-SUBSTITUTED CAMPTOTHECINS

This application is a continuation of U.S. Ser. No. 08/418,914, filed Apr. 7, 1995, now abandoned; which is a continuation of U.S. Ser. No. 08/087,147, filed Jul. 2, 1993; now abandoned; which is a continuation of U.S. Ser. No. 07/946,251, filed Sep. 16, 1992; now abandoned; which is a continuation of U.S. Ser. No. 07/589,643, filed Sep. 28, 1990; now abandoned.

FIELD OF THE INVENTION

The instant invention relates to a process for the preparation of water soluble camptothecin analogs, including methods for the preparation of intermediates thereof. The instant invention also relates to the compounds prepared by this process. Water soluble camptothecin analogs are provided which may be used for inhibiting the growth of tumor cells sensitive to such analogs.

BACKGROUND OF THE INVENTION

The separation of DNA strands is fundamental to cellular processes such as DNA replication and transcription. Since eukaryotic DNA is organized into chromatin by chromosomal proteins, the ends are constrained and the strands cannot unwind without the aid of enzymes that alter topology. Topoisomerases are enzymes that are capable of altering DNA topology in eukaryotic cells. Because of this function they are critical to the proliferation of eukaryotic cells. Topoisomerase I is a monomeric enzyme of molecular weight approximately 100,000. The enzyme binds to DNA, introduces a-transient single-strand break, unwinds the double helix (or allows this to occur) and subsequently reseals the break before dissociating from the DNA strand. Agents which inhibit the action of topoisomerase I may therefore function as anticancer agents by interfering with the proliferation of eukaryotic cells.

Camptothecin is a water-insoluble, cytotoxic alkaloid produced by *Camptotheca accuminata* trees indigenous to China and *Nothapodytes foetida*, also known as *Mappia foetida*, plants indigenous to India. Camptothecin and a few close congeners thereof are compounds known to inhibit topoisomerase I. Camptothecin and its close topoisomerase I inhibiting congeners have not proven to be suitable for clinical drug development as cytolytic agents because of lack of clinical efficacy, unacceptable dose-limiting toxicity, unpredictable toxicity, poor aqueous solubility, and/or unacceptable shelf life stability. There is a need, therefore, for antitumor agents which avoid the undesirable features of such compounds.

U.S. Pat. No. 4,604,463, issued Aug. 5, 1986 to Miyasaka et al., discloses camptothecin derivatives carrying an aminocarbonyloxy group or a chlorocarbonyloxy group in any of the 9-, 10- and 11-positions on the A ring thereof, and states that such compounds possess antitumor activity with a low level of toxicity. The camptothecin derivatives of U.S. Pat. No. 4,604,463 are disclosed therein as being prepared by treating a camptothecin derivative carrying a hydroxyl group in any of the 9-, 10- and 11-positions thereof, optionally substituted at the 7-position, with phosgene and optionally reacting the resultant chlorocarbonyloxy derivative with an amine; or, alternatively, by treating the camptothecin derivative carrying a hydroxyl group in any of the 9-, 10- and 11-positions thereof, optionally substituted at the 7-position, directly with a reactive functional derivative of a carbamic acid.

U.S. Pat. No. 4,473,692, issued Sep. 25, 1984 to Miyasaka et al., U.S. Pat. No. 4,545,880, issued Oct. 8, 1985 to Miyasaka et al., and European Patent Publication No. 0 074 256, disclose camptothecin derivatives which are indicated therein as possessing antitumor activity with a low level of toxicity. The compounds of these documents are indicated as possessing certain substituents at the 5-, 7- and 10-positions. These documents disclose methods for preparing such compounds, including methods for preparing intermediates thereof. One such method involves the preparation of 1,2,6,7-tetrahydrocamptothecin by catalytic hydrogenation of comptothecin in a solvent, such as acetic acid, dioxane-acetic acid or dioxane-hydrochloric acid, in the presence of a noble metal catalyst under atmospheric pressure. The resultant tetrahydro product is converted to 10-nitrocamptothecin in a cumbersome, multi-step sequence which includes dehydrogenation of the tetrahydro derivative with an oxidizing agent. This oxidizing agent does not introduce a hydroxyl group into the camptothecin derivative. The nitro group may be converted to a variety of related compounds using the chemistry described therein. Another method disclosed by these documents relates to the preparation of 10-hydroxycamptothecin by the photolysis of camptothecin-1-oxide by a two-step procedure.

10-Hydroxycamptothecin has been reported as having pharmacological activity. Japanese Unexamined Patent No. 59-5188 (1984) discloses a method for the preparation of 10-hydroxycamptothecin from 1,2,6,7-tetrahydrocamptothecin. The latter compound is disclosed in the Japanese Patent as being obtained by hydrogenating camptothecin in acetic acid or dioxane/acetic acid at ordinary pressure and temperature in the presence of a platinum catalyst. 10-Hydroxycamptothecin is disclosed therein as being obtained by treating 1,2,6,7-tetrahydrocamptothecin with an oxidizing agent selected from the group consisting of lead tetra acetate, CAN (cerium (IV) ammonium nitrate), Fremy's salt (potassium nitroso disulfonate, $(KSO_3)_2NO$), chromic acid or anhydride, dichromate salts, potassium permanganate and ferric chloride.

European Pat. Publication No. 0 088 642, published Sep. 14, 1983, discloses camptothecin-7-carboxamide and derivatives thereof. The compounds are taught therein as being prepared by treating camptothecin-7-carboxylic acid first with a carboxyl group-activating reagent, and then with ammonia or the corresponding amine. The European document states that such compounds are useful as intermediates in the preparation of pharmaceuticals or other classes of new camptothecin derivatives.

Wani et al., *J. Med. Chem.*, 29, 2358–2363 (1986), discloses the evaluation of several camptothecin derivatives for antitumor activity, including 9-nitro-20(S)-camptothecin, 9-amino-20(S)-camptothecin, 9-nitro-10-methoxy-20(S)-camptothecin, 9-amino-10-methoxy-20(S)-camptothecin, 9-nitro-10-hydroxy-20(S)-camptothecin and 9-acetamido-10-hydroxy-20(S)-camptothecin. Methods for preparing these compounds are also disclosed therein.

Wani et al., *J. Med. Chem.*, 23, 554–560 (1980), discloses the synthesis of various analogs of camptothecin, including an analog in which there is a diethylaminoethyl ether at C-10.

Wani et al., *J. Med. Chem.*, 30, 1774–1779 (1987), discloses the synthesis of various 11-substituted camptothecin analogs including cyano, nitro, amino, dimethylamino, formyl, aminomethyl, and hydroxymethyl. Wani et al. also teaches preparation of the various compounds. The 11-aminomethyl analog is disclosed therein as being prepared by a process wherein a solution of 11-formylcamptothecin and 2-aminoisobutyric acid in DMF was refluxed, with subsequent concentration and addition of aqueous HCl. The 11-aminomethyl analog and its hydrochloride salt, however, were reported to be inactive.

Despite the above efforts, there has remained a need for effective antitumor agents and efficient methods for their preparation.

SUMMARY OF THE INVENTION

The instant invention provides a novel process for the preparation of water soluble camptothecin analogs, including methods for the preparation of intermediates thereof. The methods disclosed herein provide, alone or together as an overall process scheme, an efficient means for obtaining such compounds.

The instant invention also provides compounds prepared by the above process, and methods for using these compounds. The compounds of the instant invention fulfill the need for topoisomerase I inhibiting agents which are attractive for clinical drug development as cytolytic agents.

Specifically, the instant invention provides an overall process for the preparation of water soluble camptothecin analogs of the following Formula (I):

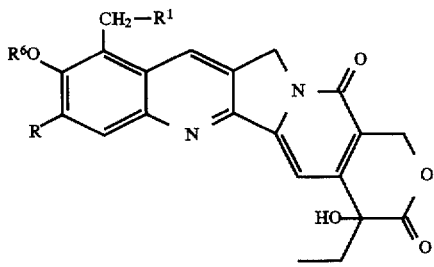

wherein:

R is hydrogen or $C_{1-6}$ alkoxy;

$R^1$ is —O—$R^2$; —S—$R^3$; or —N—($R^4$)($R^5$);

$R^2$, $R^3$, $R^4$ and $R^5$ are the same or different and are hydrogen; $C_{1-6}$ alkyl; $C_{2-6}$ hydroxyalkyl; $C_{1-6}$ dialkylamino-$C_{2-6}$ alkyl; $C_{1-6}$ alkylamino-$C_{2-6}$ alkyl; $C_{2-6}$ aminoalkyl; or a 3–7 member unsubstituted or substituted carbocyclic ring; or, when $R^1$ is —N—($R^4$)($R^5$), the $R^4$ and $R^5$ groups may be combined together with the nitrogen atom to which they are bonded to form a substituted or unsubstituted heterocyclic ring which may contain additional heteroatoms; and $R^6$ is hydrogen; a $C_{1-6}$ unsubstituted or substituted aliphatic radical; or a substituent forming, together with the oxygen atom through which it is bonded, a pharmaceutically acceptable ester group;

or a pharmaceutically acceptable salt thereof.

The compounds of Formula (I) are particularly useful as antitumor agents. The instant invention also relates to methods of using the compounds of Formula (I).

DETAILED DESCRIPTION OF THE INVENTION

The overall process for the preparation of compounds of the Formula (I) is presented in the following Scheme I. Compounds of the Formula (Ia) are compounds of the Formula (I) where $R^1$ is —N—($R^4$)($R^5$), and neither $R^4$ nor $R^5$ are hydroxyethyl. Compounds of the Formula (I) where $R^4$ or $R^5$ are hydroxyethyl may be prepared, for example, by the Mannich reaction of the compound prepared in step (2) of Scheme I with paraformaldehyde and ethanolamine in acetic acid.

Scheme I illustrates preparation of compounds where $R^6$ is hydrogen. Compounds of the Formula (I) where $R^6$ is other than hydrogen may be obtained, for example, by forming the appropriate ether or ester group subsequent to adding the 9-position substituent in step (3). Methods for forming such ether or ester groups may be chosen from those methods known to those skilled in the art.

SCHEME I

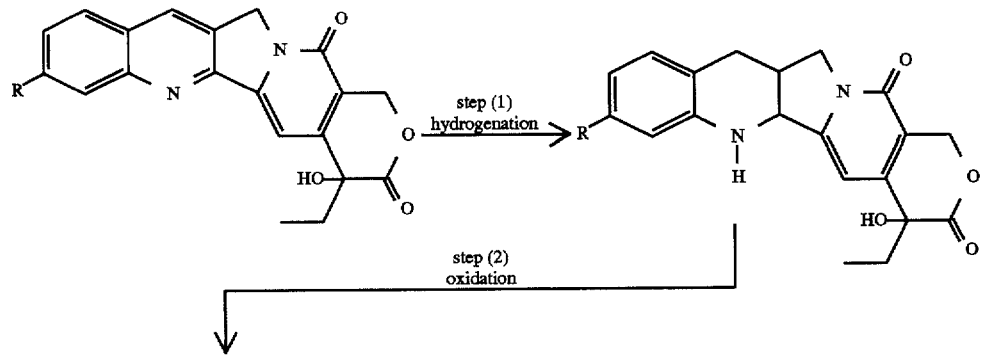

-continued
SCHEME I

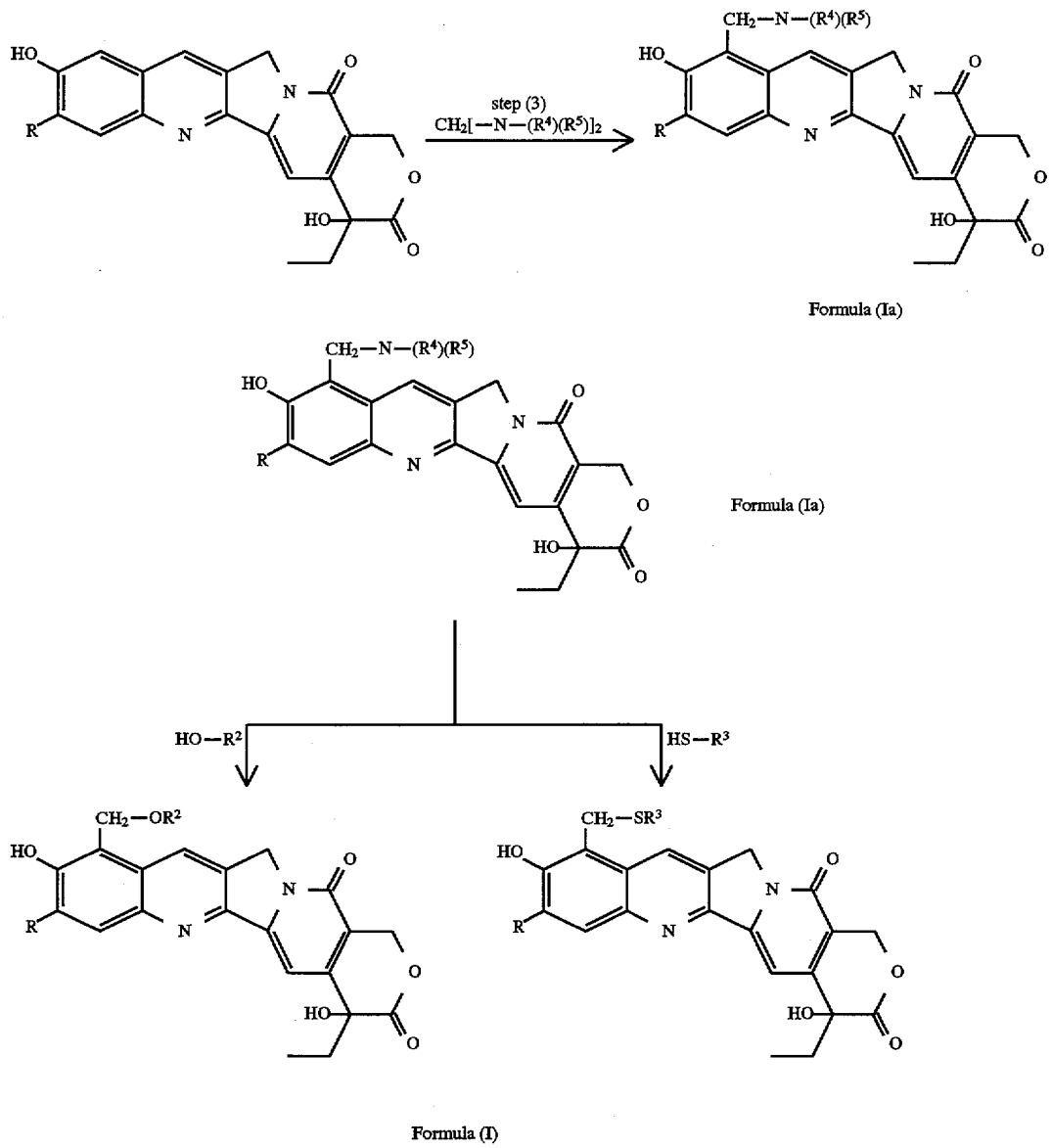

Formula (Ia)

Formula (Ia)

Formula (I)

Throughout the specification and claims, the rings are lettered, and the positions numbered, as follows.

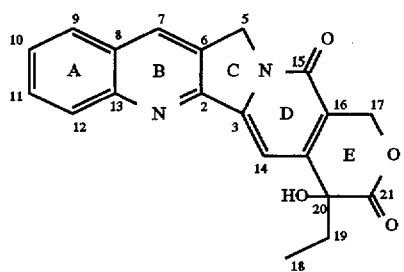

As can be seen from Scheme I, the first step of the overall process involves the conversion of camptothecin or its 11-alkoxy analog to 1,2,6,7-tetrahydrocamptothecin (hereafter, tetrahydrocamptothecin) or its 11-alkoxy analog.

The 11-alkoxycamptothecin starting material may be produced by any known method, such as by the method described in Wani et al., J. Med. Chem., 29, 2358–2363 (1986) for the synthesis of camptothecin analogs. Use of 11-methoxycamptothecin as the 11-alkoxycamptothecin is preferred in the instant invention.

The camptothecin starting material of this step is available as a naturally-produced alkaloid, as discussed above. Additionally, methods for the total synthesis of camptothecin have been reported. See, for example, Hutchinson, Tetrahedron, 37, 1047 (1981), and Suffness and Cordell, "The Alkaloids. Chemistry and Pharmacology", Brossi, A., ed., Vol. 25, Academic Press, Orlando Fla., 73 (1985), for reviews. One route for producing camptothecin which is racemic at the carbon on the 20-position is described by Wani et al., J. Med. Chem., 23, 554 (1980). The racemic camptothecin obtained by Wani et al. is purified therein by chromatography, with a subsequent crystallization from a specified medium. The medium employed by Wani et al. for crystallization is, however, a poor solvent for the purification of camptothecin from related alkaloidal impurities such that chromatography is a necessary part of the purification process.

Either naturally or synthetically produced camptothecin may be employed as the starting material in the method of the instant invention.

With respect to the 20-position, the S isomers of the starting materials are preferred.

Purification of Camptothecin or 11-Alkoxycamptothecin Starting Material

Purification of camptothecin or its 11-$C_{1-6}$ alkoxy analog by the following method yields particularly good results when these compounds are employed as starting materials in the overall process for preparing the water soluble camptothecin analogs of the instant invention. In particular, the method of purifying camptothecin or an 11-$C_{1-6}$ alkoxycamptothecin comprises a first step of contacting a mixture containing camptothecin or an 11-$C_{1-6}$ alkoxycamptothecin and impurities thereof with a solvent, wherein said solvent is capable of separating from said mixture alkaloids other than said camptothecin and 11-$C_{1-6}$ alkoxycamptothecin, as well as impurities which are capable of retarding hydrogenation of said camptothecin or 11-$C_{1-6}$ alkoxycamptothecin to their respective 1,2,6,7-tetrahydro analogs; and dissolving at least a part of said camptothecin or 11-$C_{1-6}$ alkoxycamptothecin, or said impurities, or both; and a second step of separating said camptothecin or 11-$C_{1-6}$ alkoxycamptothecin therefrom. The camptothecin or 11-$C_{1-6}$ alkoxycamptothecin separated in the second step of the purification process is preferably essentially free of impurities which are capable of retarding hydrogenation of camptothecin or 11-$C_{1-6}$ alkoxycamptothecin to their respective 1,2,6,7-tetrahydro analogs. The purification method may be repeated with the same or a different solvent to further enhance the purity of the camptothecin or 11-alkoxy analog, when desired.

The purification treatment is particularly useful in removing impurities that are difficult to eliminate at later steps of the overall process of the invention. For example, unpurified camptothecin comprising 85–87% w/w camptothecin with 9–12% impurities (HPLC, PAR (peak area ratios)) may be purified by the instant method to contain greater than 96% camptothecin (HPLC, PAR). Purified camptothecin or 11-alkoxycamptothecin may be hydrogenated more reliably to their respective tetrahydro products as compared with the unpurified compounds which contain impurities that retard hydrogenation. This is particularly true when the hydrogenation process is scaled up. Additionally, this method allows a relatively small volume of solvent to be employed while effectively removing impurities.

Preferred amounts of the solvent to be employed in the first step are from about 10 to 35 volumes of solvent per volume of camptothecin or 11-alkoxycamptothecin. Exemplary solvents which may be employed in the purification treatment of the invention include N,N-dimethylformamide, N-methylpyrrolidone, acetic acid, trifluoroacetic acid, dimethylsulfoxide, a mixture of acetic acid and dimethylsulfoxide, a mixture of ethanol and dimethylsulfoxide, and a mixture of acetic acid and hydrochloric acid.

The purification method of the invention may be used to purify either naturally-produced, or synthetic camptothecin. Solvents such as the exemplary solvents above are preferably employed. Camptothecin obtained from *Nothapodytes foetida* plants is preferably purified either from acetic acid or N,N-dimethylformamide, either by a single purification treatment or, especially by a first purification treatment using acetic acid, particularly hot acetic acid, followed by an optional second purification treatment preferably using N,N-dimethylformamide, particularly hot N,N-dimethylformamide. The second purification treatment results in a further increase in yield in a subsequent hydrogenation step. It is useful, with the camptothecin from *Nothapodytes foetida*, to add a substance to absorb impurities, such as decolorizing carbon, during the purification, preferably the purification with acetic acid. Camptothecin obtained from *Camptotheca accuminata* trees is preferably purified using N,N-dimethylformamide, particularly hot N,N-dimethylformamide. A second purification treatment, preferably from hot N,N-dimethylformamide, may be employed to enhance the purity of the camptothecin obtained.

The temperature employed for dissolution is preferably from 60° C. to the reflux temperature of the solvent, and is most preferably approximately 100° C. Cooling after dissolution may be employed to enhance purification. The camptothecin or alkoxycamptothecin may, for example, be separated in the second step of the method of the invention by a technique such as filtration.

Hydrogenation to Tetrahydrocamptothecin or its 11-Alkoxy Analog

Hydrogenation of camptothecin to tetrahydrocamptothecin has been described, for example, by Japanese Patent No. 59–5188, which, as discussed above, discloses conducting the hydrogenation reaction in acetic acid or dioxane/acetic acid at ordinary pressure and temperature in the presence of a platinum catalyst. Such a method is not fully satisfactory, however, due to the fact that the hydrogenated product is reactive. Hydrogenation therefore continues beyond the preparation of the desired tetrahydrocamptothecin product, resulting in the formation of over-reduction products. Additionally, while the use of supra-atmospheric hydrogen pressures, not disclosed by the above Japanese Patent, would be desirable from the standpoint of obtaining a more rapid reaction and/or enhanced conversion of the camptothecin starting material, it has been found that such pressures may not effectively be employed in a process such as that of the Japanese Patent due to a further increase in the formation of over-reduction products.

The instant invention provides a method of converting camptothecin or its 11-alkoxy analog to tetrahydrocamptothecin or its 11-alkoxy analog, which method comprises the step of contacting camptothecin or an 11-$C_{1-6}$ alkoxycamptothecin with hydrogen and a hydrogenation catalyst in the presence of a hydrogenation catalyst moderator, where the moderator is selected from hydrogenation catalyst poisons. The moderator employed herein mediates the reaction, allowing it to go to completion while minimizing or avoiding the formation of over-reduction products. Use of the method of the instant invention provides a substantial improvement in the substrate conversion and selectivity of the reaction. The tetrahydro products are stable with respect to further hydrogenation under reaction conditions which may include the use of supra-atmospheric hydrogen pressures and elevated temperatures.

Camptothecin or an 11-alkoxycamptothecin obtained by any method, preferably such compounds as purified by the purification method of the instant invention as discussed above, may be hydrogenated according to the method of the instant invention.

The hydrogenation catalyst moderator of the instant method may be selected from compounds known in the art to poison hydrogenation catalysts. Exemplary moderators include sulfur compounds such as dimethylsulfoxide (DMSO) or thiophene. Use of DMSO as the catalyst moderator is particularly preferred. When a sulfur compound is employed as the moderator, it may be included on the hydrogenation catalyst. Sulfided hydrogenation catalysts are exemplary of the latter.

The amount of catalyst moderator employed may be selected so that an improvement in substrate conversion and/or selectivity is obtained relative to the substrate conversion and/or selectivity obtained when the reaction is conducted in the absence of the moderator. Preferred amounts of the moderator are from about 0.2 to 5% by volume moderator, such as DMSO, per volume of reaction medium.

Suitable hydrogenation catalysts may be selected from hydrogenation catalysts known in the art. Exemplary of these are the noble metal catalysts, such as platinum, including platinum oxide ($PtO_2$) which may be pre-reduced such as by treatment under hydrogen in acetic acid; palladium; or rhodium.

The catalysts may be supported on a material such as carbon or alumina. Use of a supported catalyst may allow use of less total metal while still retaining a sufficient rate of hydrogenation, and is therefore preferred. Exemplary such catalysts include platinum on carbon, for example, 5% Pt/C, platinum on sulfided carbon, for example, 5% Pt/sulfided carbon, and platinum on alumina, for example, 5% Pt/alumina. Platinum on carbon, particularly 5% Pt/C, is particularly preferred.

The amount of hydrogenation catalyst employed may be selected so as to effect the reaction. For example, when 5% Pt/C is employed as the hydrogenation catalyst, an amount of such catalyst, including the support, which is from about 20 to 110%, particularly about 50%, by weight relative to the weight of the camptothecin or 11-alkoxycamptothecin substrate, is preferred. An amount of 5% Pt/C catalyst which contains approximately 2.5% platinum based on the weight of starting material is particularly preferred.

The conversion to the tetrahydro products may be conducted according the instant invention at a suitable hydrogen pressure, such as by the use of atmospheric hydrogen pressure. Supra-atmospheric hydrogen pressures are, however, preferably employed. At these higher pressures, the reaction proceeds more rapidly and/or provides a more complete consumption of the starting material, while avoiding the formation of over-reduction products, so that volume efficiency with a higher throughput may be achieved. Hydrogen pressures greater than about 35 psi may preferably be employed. Hydrogen pressures of from about 50 to 70 psi are particularly preferred.

An atmosphere consisting essentially of hydrogen is preferred. The reaction medium of the instant method preferably comprises a liquid phase containing a solvent in which the product is soluble and the catalyst is active, and having a volume allowing efficient mixing of the medium and good diffusion of the hydrogen reactant. An exemplary liquid forming the liquid phase is acetic acid, which is preferably employed in an amount of from about 10 to 30 volumes acetic acid per volume of camptothecin or 11-alkoxycamptothecin, with lower amounts, such as about 10 volumes, being particularly preferred. Amounts greater than 30 volumes of acetic acid per volume of starting material may be employed, although excess amounts of the liquid medium may slow the reaction.

The temperature at which the reaction is conducted is preferably from room temperature to 90° C., most preferably from 40 to 80° C. When heated, the reaction proceeds more rapidly, and goes more fully toward completion, than when conducted at room temperature.

The order of contacting the components of the reaction medium may be selected as desired.

Hydrogenation of the starting materials may produce four stereoisomers of their respective products, which differ with respect to the relative positions of the hydrogen atoms bonded to the bridgehead carbon atoms shared by the B and C rings. Production of any and all such stereoisomers is contemplated within the scope of the instant method.

The present invention also relates to the novel 11-$C_{1-6}$ alkoxy-1,2,6,7-tetrahydrocamptothecin intermediates prepared herein. The novel intermediates may be prepared by a method comprising the step of contacting an 11-$C_{1-6}$ alkoxycamptothecin with hydrogen and a hydrogenation catalyst, and, preferably, by the further use of a hydrogenation catalyst moderator as discussed above.

Isolation of the tetrahydro products may be conducted by an appropriate method, for example, the purification procedure described in Japanese Patent No. 59-5188. In particular, the catalyst is filtered off, and the filtrate is evaporated to dryness in vacuo. The residue is dissolved in methylene chloride, washed, dried, evaporated, and chromatographed on silica gel to give the tetrahydro product. A preferred method comprises filtration to remove the hydrogenation catalyst, which may be followed immediately by the next step of the overall reaction scheme, that is, the conversion of the tetrahydro products to their 10-hydroxy analogs described as follows.

Oxidation to 10-Hydroxycamptothecin or its 10-Hydroxy-11-Alkoxy Analog

The second step of the overall process of Scheme I involves the conversion of tetrahydrocamptothecin or its 11-alkoxy analog to 10-hydroxycamptothecin or its 10-hydroxy-11-alkoxy analog. The starting materials of this step are preferably obtained by the hydrogenation method of the instant invention described above.

The conversion of tetrahydrocamptothecin to 10-hydroxycamptothecin has been described in Japanese Patent No. 59-5188, which, as discussed above, discloses the use of an oxidative agent selected from the group consisting of lead tetra acetate, CAN (cerium (IV) ammonium nitrate), Fremy's salt (potassium nitroso disulfonate, $((KSO_3)_2NO)$, chromic acid or anhydride, dichromate salts, potassium permanganate and ferric chloride. The Japanese patent indicates that solvents used for this treatment include acetic acid, methanol, ethanol, chloroform, pyridine, benzene, methylene chloride, dioxane, THF, water and trifluoroacetic acid, and mixtures thereof. The process of the Japanese Patent has been found, however, to be disadvantageous in that the oxidation is not highly selective, forming, in addition to 10-hydroxycamptothecin, substantial amounts of unwanted camptothecin which must be separated from the ultimate product. The 10-hydroxycamptothecin product itself is also reactive and tends to be destroyed during the process of the Japanese Patent. Additionally, the use of an oxidative agent such as lead tetra acetate may result in heavy metal contamination of the ultimate product.

The instant invention provides a method for oxidizing tetrahydrocamptothecin or its 11-$C_{1-6}$ alkoxy analog to 10-hydroxycamptothecin or its 10-hydroxy-11-alkoxy analog, comprising the step of contacting tetrahydrocamptothecin or an 11-$C_{1-6}$ alkoxytetrahydrocamptothecin with an oxidizing agent in a liquid reaction medium, wherein (a) the liquid reaction medium comprises a liquid selected so that at least part of the 10-hydroxycamptothecin or 10-hydroxy-11-alkoxycamptothecin product formed precipitates during said reaction, with the proviso that when tetrahydrocamptothecin is employed as the starting material and an oxidizing agent (b) as follows is not employed, the liquid employed as the liquid reaction medium (a) does not consist of methanol; and/or (b) the oxidizing agent is potassium persulfate, iodosobenzene, an ester of iodosobenzene, sodium periodate or potassium periodate. When tetrahydrocamptothecin is employed as the starting material and an oxidizing agent (b) is not employed, the liquid reaction medium (a) above preferably does not consist of any of methanol, ethanol, chloroform, benzene, methylene chloride, dioxane or water, taken alone.

Use of the liquid reaction medium described in (a) above is advantageous in that the 10-hydroxy- or 10-hydroxy-11-alkoxycamptothecin products precipitate out and are thus essentially isolated, minimizing or eliminating further reaction of the desired products. By use of such a medium, the formation of camptothecin or 11-alkoxycamptothecin as an unwanted by product may be minimized or avoided. In addition, the formation through over-oxidation of compounds other than the desired products may thus be minimized or avoided in the post-reaction medium, thereby providing a greatly increased product yield.

It is preferred to employ a liquid reaction medium (a) comprising a mixture of water and an organic solvent to achieve precipitation. The liquid medium (a) comprising a mixture of water and an organic solvent may be obtained, for example, by mixing water with an organic liquid exemplified by acetic acid, acetone, N,N-dimethylformamide, or a low molecular weight alcohol such as methanol, ethanol or isopropanol, in relative amounts to form a liquid composition in which at least part of the 10-hydroxycamptothecin or 10-hydroxy-11-alkoxy analog formed precipitates.

By the term a "low molecular weight alcohol" above and elsewhere herein is meant an alcohol which is liquid at the temperature at which it is employed, preferably a $C_1$–$C_4$ alcohol.

Preferred compositions for the liquid employed as the reaction medium include those compositions containing water and an organic solvent where the amount of water represents from about 25 to 75% by volume, based on the total volume of the liquid. Especially preferred is an approximately 1:1 volume ratio of water to a solvent such as acetic acid, acetone, N,N-dimethylformamide, or a low molecular weight alcohol.

Preferably, the product compounds are essentially insoluble in the liquid reaction medium (a) of the invention.

An additional advantage is obtained when water is used in conjunction with acetic acid as the liquid medium. When acetic acid alone is used, both 10acetoxycamptothecin or its 10-acetoxy-11-alkoxy analog and 10-hydroxycamptothecin or its 10-hydroxy-11-alkoxy analog are formed, the former acetoxy compounds being formed in a substantial quantity. The addition of water minimizes or avoids entirely the amount of such acetoxy compounds found in the post-reaction medium, so that a separate hydrolysis step for the conversion of these compounds to 10-hydroxycamptothecin or its 10-hydroxy-11-alkoxy analogs may be eliminated, if desired.

The oxidizing agents (b) above are advantageous in that they are sufficiently mild so as to result in little or no destruction of the 10-hydroxy- or 10-hydroxy-11-alkoxycamptothecin products through further oxidation. Particularly preferred of the oxidizing agents (b) above are the esters of iodosobenzene, for example, those esters having the formula $PhI(OR^7)_2$, where Ph is phenyl; $R^7$ in each —$OR^7$ group may be the same or different and is hydrogen, —C(O)—$R^8$ or —$SO_2$—$R^9$; $R^8$ and $R^9$ and are unsubstituted or substituted hydrocarbon radicals; and where $R^7$ in at least one of the —$OR^7$ groups is other than hydrogen. Exemplary such esters are iodobenzene(bis)trifluoroacetate, formed by esterifying iodosobenzene with trifluoroacetic acid, iodobenzenediacetate, formed by esterifying iodosobenzene with acetic acid, and hydroxy(tosyloxy) iodobenzene, formed by esterifying iodosobenzene with toluene sulfonic acid. Most preferred of these is iodobenzenediacetate ($PhI(OC(O)CH_3)_2$).

It is preferred to employ an oxidizing agent as described in (b) above, especially iodobenzenediacetate, when employing the liquid medium described in (a) above, as particularly good results are obtained by use of this combination.

The amount of oxidizing agent may be selected to effect the reaction. Amounts greater than about two (2) equivalents of oxidant relative to the tetrahydrocamptothecin or 11-alkoxy analog thereof are preferred. An amount of oxidant relative to tetrahydrocamptothecin or its 11-alkoxy analog of approximately three (3) equivalents is most preferred. When employing an oxidizing agent (b) as described above, a liquid medium such as N,N-dimethylformamide, acetone, a low molecular weight alcohol, or, preferably, acetic acid, may be employed, although the liquid medium described in (a) above is most preferred.

The loading of the tetrahydro starting material is preferably from about 2 to 10%, especially from about 5 to 10%, by weight based on the weight of the liquid medium. Suitable pressures and temperatures for conducting the reaction may be selected, with atmospheric pressure and ambient temperature being preferred. The reaction may be conducted under an atmosphere of air.

The present invention also relates to the novel 10-hydroxy-11—$C_{1-6}$ alkoxycamptothecin intermediates prepared herein. These novel intermediates may be prepared by a method comprising the step of contacting an 11—$C_{1-6}$ alkoxy-1,2,6,7-tetrahydrocamptothecin with an oxidizing agent in a liquid reaction medium, and, preferably, by the method discussed above.

Preparation of Compounds of Formula (I)

Compounds of the Formula (I) are prepared beginning in the third step of the overall process of Scheme I above. The 10-hydroxycamptothecin or 10-hydroxy-11-alkoxycamptothecin starting materials of this step are preferably obtained by the oxidation method described above. Starting materials otherwise obtained may, however, be employed. For example, 10-hydroxycamptothecin is a naturally-produced compound, which may be found in the same plant as camptothecin. 10-Methoxycamptothecin, which has also been isolated from the same plant as camptothecin, may be converted to 10-hydroxycamptothecin by refluxing with hydrogen bromide. 10-Hydroxycamptothecin may also be obtained by the method of Japanese Patent Application No. 59-5188, discussed above, by reduction of the pyridine ring of camptothecin, followed by oxidation with lead tetra acetate. Further, racemic 10-hydroxycamptothecin may be prepared by the method of Wani et al., *J. Med. Chem.*, 23,554 (1980).

The instant invention provides a method for the preparation of compounds of the Formula (I) in which the starting material undergoes the reaction rapidly, and may be substantially consumed. In particular, the instant invention provides a method for preparing a compound of the Formula (Ib), or a pharmaceutically acceptable salt thereof, the compound of the Formula (Ib) having the following structure:

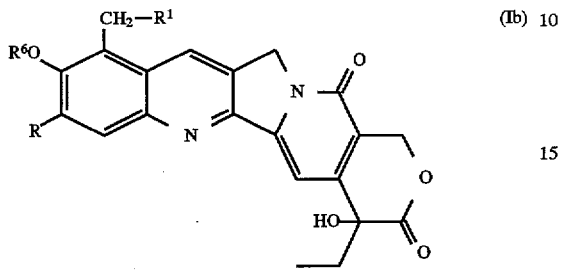

wherein:

R is hydrogen or $C_{1-6}$ alkoxy;

$R^1$ is —O—$R^2$; —S—$R^3$; or —N—($R^4$)($R^5$);

$R^2$, $R^3$, $R^4$ and $R^5$ are the same or different and are hydrogen; $C_{1-6}$ alkyl; $C_{3-6}$ hydroxyalkyl; $C_{1-6}$ dialkylamino-$C_{2-6}$ alkyl; $C_{1-6}$ alkylamino-$C_{2-6}$ alkyl; $C_{2-6}$ aminoalkyl; or a 3–7 member unsubstituted or substituted carbocyclic ring; or, when $R^1$ is —N—($R^4$)($R^5$), the $R^4$ and $R^5$ groups may be combined together with the nitrogen atom to which they are bonded to form a substituted or unsubstituted heterocyclic ring which may contain additional heteroatoms; and $R^6$ is hydrogen; a $C_{1-6}$ unsubstituted or substituted aliphatic radical; or a substituent forming, together with the oxygen atom through which it is bonded, a pharmaceutically acceptable ester group;

comprising:

(i) preparing a compound of the Formula (Ib), or a pharmaceutically acceptable salt thereof, in which $R^1$ is an amine group —N—($R^4$)($R^5$) and $R^6$ is hydrogen, by contacting 10-hydroxycamptothecin or a 10-hydroxy-11—$C_{1-6}$ alkoxycamptothecin with a compound of the Formula (II), the compound of the Formula (II) having the following structure:

$$CH_2[-N-(R^4)(R^5)]_2 \qquad (II)$$

where $R^4$ and $R^5$ are as defined above for Formula (Ib); and (ii) optionally, (a) preparing a compound of the Formula (Ib), or a pharmaceutically acceptable salt thereof, in which $R^1$ is —O—$R^2$ or —S—$R^3$, by converting the amine group of the compound prepared in step (i) to —O—$R^2$ or —S—$R^3$; and/or (b) preparing a compound of the Formula (Ib), or a pharmaceutically acceptable salt thereof, in which $R^6$ is other than hydrogen, by converting the 10-position hydroxyl group of the compound prepared in step (i) to the group —O$R^6$ where $R^6$ is with the exception of hydrogen, as defined above for Formula (Ib).

In step (ii) (a) of the above method of the invention, those compounds where $R^1$ is —O—$R^2$ or —S—$R^3$ may be prepared, for example, by heating a compound as prepared in step (i) above with an appropriate alcohol of the formula HO—$R^2$ or thiol of the formula HS—$R^3$ where $R^2$ and $R^3$ are as defined in Formula (Ib), in an inert solvent such as N,N-dimethylformamide. Where preparation of a compound having, as $R^1$, a group —O—$R^2$ or —S—$R^3$ is contemplated, it is preferred to prepare, in step (i), a compound having, as $R^1$, the group —N($CH_3$)$_2$. When the compound prepared in step (i) is a free base, a small amount of strong acid, such as hydrochloric acid, may be added in step (ii) (a). Step (ii) (a) may be conducted simultaneously with, or subsequent to, step (i). The steps may be conducted simultaneously to prepare a compound where $R^1$ is —O—$R^2$ or —S—$R^3$, for example, by including the appropriate alcohol or thiol in the reaction mixture of step (i), and either a strong acid is added to the reaction mixture or the amine group is in the form of a strong acid Salt. Step (ii) (b) may be conducted subsequent to step (i).

With respect to $R^6$, exemplary $C_{1-6}$ unsubstituted or substituted aliphatic radicals include straight and branched chain aliphatic radicals, and are preferably unsubstituted or substituted $C_{1-4}$ alkyl radicals. Exemplary pharmaceutically acceptable esters include those where $R^6$ is a $C_{1-6}$ unsubstituted or substituted, straight or branched chain, aliphatic carbonyl radical, preferably a $C_{1-4}$ unsubstituted or substituted alkyl carbonyl radical.

By the term "carbocyclic ring" is meant a fully saturated, partially saturated or fully unsaturated ring system.

Preferred compounds of Formula (Ib) include those where $R^1$ is dimethylamino, N-morpholino, N-methylpiperazinyl, (4'-piperidine)N-piperidinyl, cyclohexylamino, N-methylanilino, ethoxy, cyclopropylamino, N,N-dimethylaminoethoxy, N,N-dimethylaminoethylthio, N,N-dimethylaminoethylamino, or methylamino. Especially preferred are the compounds of the Formula (Ib) in which $R^1$ is dimethylamino or N-morpholino, particularly dimethylamino, and the hydrochloride and acetate salts thereof.

The relative amounts of the reactants in step (i) may be selected to effect the reaction. Preferably, an excess of the compound of Formula (II) is employed, such as an amount equal or in excess of 1.2 equivalents of the Formula (II) compound relative to the 10-hydroxy- or 10-hydroxy-11-alkoxycamptothecin starting material.

The temperature employed in conducting the reaction with the compound of Formula (II) is preferably between 0° C. and the reflux temperature of the solvent, most preferably, ambient temperature. Use of ambient temperature minimizes thermal decomposition of the relatively less stable Formula (Ib) compounds, such as those in the free base form or in the acetate salt form resulting, for example, when acetic acid is employed as the solvent. Atmospheric pressure is preferred. The reaction may be conducted under an air atmosphere.

The method of the invention for the preparation of compounds of the Formula (Ib) may be conducted in a solvent, such as acetic acid. The loading of the 10-hydroxy- or 10-hydroxy-11-alkoxy starting material is preferably from about 4 to 10% by weight based on the weight of the solvent.

A preferred embodiment of the method of the invention comprises, particularly in step (i), the use of a solvent selected from those solvents comprising acetonitrile or a low molecular weight alcohol. The acetonitrile or low molecular weight alcohol solvent may be mixed with one or more other organic liquids. When acetonitrile is employed as the solvent, it may, for example, be used alone or in a mixture with a low molecular weight alcohol or an inert, chlorinated hydrocarbon such as methylene chloride. When a low molecular weight alcohol is employed as the solvent, it may, for example, be used alone or in a mixture with an inert, chlorinated hydrocarbon.

The use of a mixture of a low molecular alcohol and an inert chlorinated hydro carbon as the solvent is preferred. Particularly preferred is the use of a mixture of a low molecular weight alcohol such as 1-propanol and methylene chlorine, most preferably at a ratio of about 5 parts of alcohol to about 10 parts of methylene chloride by volume.

Use of the preferred solvent system in preparing compounds of the Formula (Ib) provides advantages as compared with the use of a solvent such as acetic acid, for example, in that the reaction may be run without an acid, allowing direct isolation of an acid salt without a salt exchange, and the yield of recovered product may be increased, for example, by more complete consumption of the starting material. Where it is desired to obtain a given salt, direct addition of the appropriate acid, alone or in solution, may be employed. Additionally, by using the above preferred solvent system, camptothecin, an impurity formed, for example, during the above oxidation step, may be removed in the mother liquors, increasing the purity of the isolated product.

Compounds of the Formula (I) may be employed in the recrystallization method described below. Compounds of the Formula (Ib) do not include compounds of the Formula (I) where $R^2$, $R^3$, $R^4$ or $R^5$ are a hydroxyethyl group. The latter compounds may be obtained by the method of European Patent No. 0 321 122, incorporated herein by reference.

It is recognized that due to the asymmetric carbon atom in the E ring of the compounds of Formula (I), that is, carbon atom number 20, optical isomers will exist. The S-isomer is the preferred isomer, although the R-isomer and racemic mixture (racemate) are also included within the scope of the compounds of Formula (I).

Pharmaceutically acceptable salts and methods for their preparation may be selected by those skilled in the art. Preferred pharmaceutically acceptable salts of compounds of the Formula (I) include acetate, methane sulfonate and, especially, hydrochloric, such as mono- and dihydrochloride. The dihydrochloride salt may be formed by addition of excess hydrochloric acid, and likely results from protonation of the quinoline nitrogen in the B ring, as well as a nitrogen of the $R^1$ group. Exemplary pharmaceutically acceptable salts also include quaternary ammonium salts, which may, for example, be obtained by treating the compound obtained in step (i) of the above method with an alkylating agent. A preferred such salt is the compound of Formula (I) where the 9-position substituent is —$CH_2$—$N(CH_3)_3^+$. Exemplary pharmaceutically acceptable anions of quaternary salts of compounds of the Formula (I) include methane sulfonate and chloride.

The present invention also relates to novel compounds of the Formula (I) where R is $C_{1-6}$ alkoxy.

Purification and Isolation of Water Soluble Camptothecin Analogs

The compounds of the Formula (I), or pharmaceutically acceptable salts thereof, obtained, for example, as above may be purified and isolated by methods such as column chromatography and lyophilization or stripping. Preferably, however, a compound having the structure of the following Formula (I):

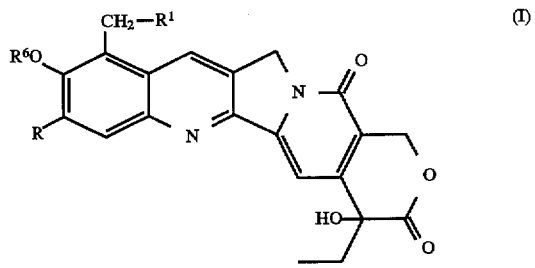

wherein:

R is hydrogen or $C_{1-6}$ alkoxy;

$R^1$ is —O—$R^2$; —S—$R^3$; or —N—$(R^4)(R^5)$;

$R^2$, $R^3$, $R^4$ and $R^5$ are the same or different and are hydrogen; $C_{1-6}$ alkyl; $C_{2-6}$ hydroxyalkyl; $C_{1-6}$ dialkylamino-$C_{2-6}$ alkyl; $C_{1-6}$ alkylamino-$C_{2-6}$ alkyl; $C_{2-6}$ aminoalkyl; or a 3–7 member unsubstituted or substituted carbocyclic ring; or, when $R^7$ is —N—$(R^4)$ $(R^5)$, the $R^4$ and $R^5$ groups may be combined together with the nitrogen atom to which they are bonded to form a substituted or unsubstituted heterocyclic ring which may contain additional heteroatoms; and $R^6$ is hydrogen; a $C_{1-6}$ unsubstituted or substituted aliphatic radical; or a substituent forming, together with the oxygen atom through which it is bonded, a pharmaceutically acceptable ester group;

or a pharmaceutically acceptable salt thereof, is purified and isolated by a method comprising the steps of:

(a) adding a first liquid, which liquid is a solvent for the compound, in an amount such that at least part of the compound is dissolved to form a solution or a slurry;

(b) subsequent to step (a), adding a second liquid to the solution or slurry obtained in step (a), which liquid facilitates recrystallization of the compound dissolved therein, and recrystallizing the compound; and (c) collecting by filtration the compound of Formula (I) or salt thereof.

Steps (a) through (c) of the instant method are preferably conducted at a temperature which essentially avoids instability of the compound of Formula (I) or a salt thereof.

The purification method of the instant invention provides savings in both cost and labor as compared, for example, with purification by chromatography. The product obtained by the instant method is also purer than that obtained by chromatography. Isolating the product by filtration saves time and labor as compared, for example, with lyophilization, and the product is more easily handled than a lyophilized product. Additionally, the salt content, such as the chloride content, of the product material may be adjusted during the instant method. The chloride content of the crude product may, for example, vary from <100% to >200% of theory for the monohydrochloride, and may be adjusted to a value approximately that of the monohydrochloride.

The solvent employed in step (a) may be any solvent which, in sufficient amount, dissolves at least part of the compound of Formula (I) or a salt thereof to form a solution or a slurry. Preferably, the nature and quantity of the solvent are selected for essentially complete dissolution. Gentle heating may be used during step (a), preferably heating at a temperature which essentially avoids instability of the compound, such as a temperature below approximately 40° C. Dissolution at room temperature is most preferred. It is preferred to employ from about 3 to 15 volumes of solvent per volume of compound to be purified.

Water is the preferred solvent of step (a), although organic solvents or mixtures of water and miscible organic solvents may be employed. Dilute hydrochloric acid may also be employed.

Filtration is preferably performed subsequent to step (a) to remove any undesired, insoluble material present. The filtration may be performed by methods known to those in the art. The solution or slurry obtained in step (a), or the filtrate thereof when a filtration step is conducted subsequent to step (a), is preferably concentrated, such as by use of a vacuum. Concentration at room temperature is preferred.

In step (b), a liquid is added which facilitates recrystallization of the solution or slurry. It is preferable to maintain the temperature below 40° C. during this step, most preferably at room temperature. Preferred amounts of the liquid added in step (b) are from about 15 to 60 volumes of liquid per volume of compound to be purified. Exemplary liquids to be added in step (b) include acetone, acetonitrile, lower alcohols such as methanol, ethanol, 1-propanol, or 2-propanol, or tetrahydrofuran, with 1-propanol or acetone being preferred. Addition of the solvent in step (a), followed by the subsequent addition of the liquid in step (b), provides advantages as compared with, for example, simultaneous addition of these liquids. Dissolution in step (a) may be accomplished more rapidly and more completely, allowing use of a filtration step to remove insoluble impurities. In addition, the enhanced dissolution in step (a) obtained by successive addition allows the dissolution step to be performed at relatively low temperatures, thus minimizing or avoiding decomposition of the compound to be purified.

The recrystallized mixture is preferably stirred and/or cooled to fully precipitate the product compound, which is then collected by filtration. The product may be dried, for example, under a vacuum and/or with heating.

The water soluble camptothecin analogs of Formula (I), or salts thereof, may be used in an amount effective to inhibit the growth of tumor cells sensitive to such an analog in an animal in need thereof, and in pharmaceutical compositions capable of such inhibition. Cytotoxic compounds of Formula (I) are potent inhibitors of purified topoisomerase I. The pharmaceutical compositions may contain an effective, tumor cell growth-inhibiting amount of a compound of the Formula (I), or a salt thereof, and an inert pharmaceutically acceptable carrier or diluent.

A compound of the Formula (I), or a salt thereof, is administered in conventional dosage form prepared by combining a therapeutically effective amount of the compound ("active ingredient") with standard pharmaceutical carriers or diluents according to conventional procedures. These procedures may involve mixing, granulating and compressing or dissolving the ingredients as appropriate to the desired preparation. The pharmaceutical compositions may be prepared in dosage unit form appropriate for parenteral or oral administration.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary liquid carriers are syrup, peanut oil, olive oil, water and the like. Similarly, the carrier or diluent may include time delay material well known to the art, such as glyceryl monostearate or glyceryl distearate alone or with a wax, ethylcellulose, hydroxypropylmethylcellulose, methylmethacrylate and the like.

A wide variety of pharmaceutical forms may be employed. Thus, if a solid carrier is used, the preparation can be tableted, placed in a hard gelatin capsule in powder or pellet form or in the form of a troche or lozenge. The amount of solid carrier may vary widely but preferably will be from about 25 mg to about 1 g. If a liquid carrier is used, the preparation may be in the form of a syrup, emulsion, soft gelatin capsule, sterile injectable solution or suspension in an ampule or vial or nonaqueous liquid suspension.

To obtain a stable water soluble dose form, a pharmaceutically acceptable salt of a compound of Formula (I) is dissolved in an aqueous solution of an organic or inorganic acid, such as 0.3M solution of succinic acid, or, preferably, citric acid. If a soluble salt form is not available, the compound of Formula (I) is dissolved in a suitable cosolvent or combinations thereof. Examples of such suitable cosolvents include, but are not limited to, alcohol, propylene glycol, polyethene glycol 300, polysorbate 80, glycerin and the like in concentrations ranging from 0–60% of the total volume.

The composition may also be in the form of a solution of a salt form of the active ingredient in an appropriate aqueous vehicle such as water or isotonic saline or dextrose solutions. For those Formula (I) compounds which do not have a basic side-chain in the 9-position, an alkali metal salt, such as the sodium salt, of the carboxylate formed on alkaline hydrolysis of the E-ring lactone would yield a soluble salt.

It will be appreciated that the actual preferred dosages of the Formula (I) compounds used in the compositions of this invention will vary according to the particular complex being used, the particular composition formulated, the mode of administration and the particular site, host and disease being treated. Optimal dosages for a given set of conditions may be ascertained by using conventional dosage determination tests.

For parenteral administration of compounds of the Formula (I), the dosage level generally employed is up to an expected amount of about 20 mg/m$^2$ of body surface area per day for one to five days. However, dosage amounts may be higher in practice. Preferably, the administration is repeated about every fourth week for four courses of treatment. For oral administration, the dosage level generally employed is up to an expected amount of about 20 mg/m$^2$ of body surface area per day for one to five days, with courses of treatment repeated at appropriate intervals. However, dosage amounts may be higher in practice.

A method for inhibiting the growth of animal tumor cells sensitive to a compound of Formula (I), or a salt thereof, comprises administering to a host animal afflicted with said tumor cells an effective tumor growth-inhibiting amount of such compound. During the course of treatment the active ingredient may be administered parenterally or orally on a daily basis in an amount having a general expected upper limit of about 20 mg/m$^2$ of body surface area for one to five days, with courses of treatment repeated at appropriate intervals, as discussed above. Dosage amounts may be higher in practice.

The following Examples are merely illustrative of the invention, and should not be construed as limiting the scope thereof in any way.

EXAMPLE 1

Recrystallization of Camptothecin (Chinese Material)

31.1 grams of (20 S) camptothecin were dissolved in 620 ml of N,N-dimethylformamide at approximately 155° C. with vigorous stirring. The solution was cooled slowly to ambient temperature. After stirring until crystallization was complete, the suspension was filtered to give a light-yellow solid. Analysis by HPLC showed about 98% camptothecin with two small impurities (about 1% each) with a longer retention time than camptothecin. The sample was washed with methanol and air dried. The recovery of dried material was 24.9 g, m.p. 263°–265° C. (91% corrected for assay).

EXAMPLE 2

Recrystallization of Camptothecin (Chinese Material)

301 grams of crude camptothecin were suspended with stirring in 3000 ml of N,N-dimethylformamide. The mixture was stirred at approximately 100° C. for about 14 hours, and cooled slowly to ambient temperature with stirring. The solid was collected by an appropriate method and washed with methanol. After drying to a constant weight of 250 g the product was slurried for >12 hours with 2500 ml (10 vols. v/w) of N,N-dimethylformamide at 100° C. The suspension was slowly cooled with stirring to ambient temperature. The product was collected, washed with methanol and dried to a constant weight of 236 g (86% overall recovery corrected for assay) m.p. 263°–265° C.

EXAMPLE 3

Recrystallization of Camptothecin (Indian Material)

291 grams of (20 S) camptothecin were dissolved by stirring with 10.2 liters of acetic acid with heating to reflux. About 10% by weight of activated charcoal (29 grams) was added, and the hot suspension was filtered through Celite. The resulting mixture was concentrated by distillation to a volume of about 5.8 liters. After cooling to ambient temperature with stirring, the solid product was collected, washed with methanol and dried to a constant weight. 230 grams of material were recovered. The sample assayed 98% by weight for camptothecin content as determined by HPLC.

A portion (23.4 g) of the sample of (20 S) camptothecin purified in the above manner was stirred with 234 ml of N,N-dimethylformamide at 100° C. for about 24 hours. The suspension was cooled to ambient temperature with stirring, and the solid camptothecin was collected by filtration. After washing with methanol and drying to a constant weight the product assayed >99% for camptothecin by HPLC.

EXAMPLE 4

Recrystallization of Camptothecin (Chinese Material)

1500 g of a Chinese sample of (20 S) camptothecin were stirred with 15.0 liters of N,N-dimethylformamide at 100° C. for 24 hours. The slurry was cooled with stirring to ambient temperature over 24 hours, filtered, and washed with 2×7.5 liters of methanol to give a light-yellow solid. The solid was dried under vacuum. 1277 g of material were recovered.

1277 g of (20 S) camptothecin from the above procedure were stirred with 12.8 liters of N,N-dimethylformamide at 100° C. for 24 hours. The slurry was cooled to ambient temperature with stirring over 24 hours, filtered and washed with 2×6.4 liters of methanol. The pale yellow solid was dried under vacuum. 1197 g of material were recovered. The product assayed at >99% by weight for camptothecin content as determined by HPLC versus a standard sample of material.

EXAMPLE 5

Preparation of 10-Hydroxycamptothecin
(a) Preparation of Tetrahydrocamptothecin A 5-gallon, stainless steel, high pressure, stirred autoclave was charged with a slurry containing 1000 grams of camptothecin in glacial acetic acid. 500 grams of 5% platinum-on-carbon slurried with glacial acetic acid were added to the reactor, such that a total of about 10 liters of acetic acid (10 volumes v/w versus camptothecin) was used in the reaction. 75 ml of dimethyl sulfoxide were added, and the reactor was sealed. After purging with nitrogen, the stirred reactor was charged with hydrogen to a pressure of approximately 70 psi. This approximate pressure of hydrogen was maintained throughout the subsequent reduction. The reactor was gradually heated to a temperature of about 65° C., and the uptake of hydrogen was carefully monitored. After about 6 hours the uptake of hydrogen had essentially stopped, although the reaction could safely be continued for a minimum of 24 hours with no decrease in the yield of product being observed. The reaction was cooled to about 30° C., vented to the atmosphere and removed from the reactor. The reactor was washed with about 11 liters of glacial acetic acid. The total volume of acetic acid was filtered to remove suspended catalyst, and the combined volumes were assayed by HLPC to determine the content of tetrahydrocamptothecin (approximately 874 g, 89% yield). After assay was complete, the product in acetic acid solution was oxidized directly as described.

(b) Preparation of 10-Hydroxycamptothecin

Approximately one-half of the acetic acid solution of tetrahydrocamptothecin described above (about 10.4 liters solution volume containing approximately 398 g, 1.13 mole of tetrahydrocamptothecin) was charged to a 22-liter, stirred glass vessel. The solution was concentrated by distillation to about 40% of its original volume (4 liters). The solution was diluted with an equal amount of distilled water and allowed to stir at approximately 20° C. A heavy, white, precipitate suspension resulted. The suspension was stirred rapidly while 728 g (2.0 eq) of iodobenzenediacetate were quickly added. A slight exotherm to about 35° C. was observed. An additional 400 g (1.1 eq) of iodobenzenediacetate were added in three approximately equal portions at hourly intervals. The suspension was stirred for about 14 hours after addition was complete. The suspension was distilled, and a total of 6 liters of 1:1 acetic acid:water was added in several portions so as to maintain an approximately constant volume for the initial portion of the distillation. After about 12 liters of solvent had been collected the distillation was stopped and the suspension was stirred at ambient temperature for approximately 16 hours. The product was collected and washed with methanol. The product was dried to a constant weight of 398 g (88% yield, corrected for assayed content). The product, m.p. 267°–268° C., contained approximately 1% camptothecin.

EXAMPLE 6

Preparation of 10-Hydroxycamptothecin 1720 ml of water were slowly added to a solution of 172 grams of (20 S) tetrahydrocamptothecin in 1720 ml of acetic acid. At the end of the addition, a thick, cream-colored slurry which was difficult to stir was obtained.

314 grams (2.0 equivalents) of iodobenzenediacetate were added with rapid stirring over approximately 6 minutes. The slurry turned dark green as nearly all of the precipitate dissolved. Over a few minutes the color of the slurry faded to yellow as more precipitate formed. The temperature rose to a maximum of 36° C. Stirring was continued for one hour at room temperature. At this time an additional 79 grams (0.5 equivalent) of iodobenzenediacetate were added over 1 minute. The slurry was stirred for an additional (1) hour with no significant exotherm. At this time 63 grams (0.4 equivalent) additional iodobenzenediacetate were added with continued stirring. After an additional 1.5 hours 16 grams (0.1 equivalent) of iodobenzenediacetate were added for a total addition of 3.0 equivalents of oxidant.

The slurry was stirred at room temperature for 18 hours. The mixture was then heated to distill the solvent at atmospheric pressure. A total of 5160 ml of a 1:1 solution of acetic acid:water was periodically added to maintain an approximately constant volume through most of the distillation. The slurry was eventually concentrated to a final volume of approximately 1720 ml. The initial distillate removed was cloudy and separated into two phases upon collection. The heavier phase of the distillate consisted of mostly iodobenzene. Distillation was stopped and the yellow slurry was stirred at room temperature to cool over 24 hours. The solid was collected by filtration and rinsed twice with 860 ml portions of methanol, followed by removal of methanol by filtration. The collected solid was dried under vacuum. After drying, 171 g of product were obtained (91% isolated yield, corrected for the purity of the product as determined by HPLC assay versus a standard sample of material). The isolated product contained approximately 1% camptothecin as a by product.

EXAMPLE 7

Preparation of (20 S) 9-N,N-Dimethylaminomethyl-10-Hydroxycamptothecin Hydrochloride Salt A 22 liter flask was charged with 428 g of 10-hydroxycamptothecin. After the addition of 4280 ml of methylene chloride and 2140 ml of 1-propanol, the stirred suspension was charged with 259 g of bis(dimethylamino) methane added over about 5 minutes. The suspension was stirred with periodic monitoring by HLPC for the presence of starting material. After 5 hours no detectable (<0.1%) starting material remained. After about 6 hours reaction time 514 g of concentrated, aqueous hydrochloric acid in 214 ml of 1-propanol was added continuously over about 2 hours. Stirring was continued for about 16 hours. The product was collected by filtration and washed with methylene chloride. The product was dried to a constant weight to give 415 g (91% yield) of the title compound.

EXAMPLE 8

Preparation of (20 S) 9-N,N-Dimethylaminomethyl-10-Hydroxycamptothecin Acetate Salt 2.60 mmoles of (20 S) 10-hydroxycamptothecin are combined with 6.08 mmoles of bis(dimethylamino)methane in 15.45 ml of acetic acid. The title compound is isolated after reaction.

EXAMPLE 9

Preparation of (20 S) 9-Morpholinomethyl-10-Hydroxycamptothecin Acetate Salt

The title compound is prepared by the method of Example 8, by substituting bis(N-morpholino)methane for bis(dimethylamino)methane.

EXAMPLE 10

Preparation of (20 S) 9-N-Methylpiperazinylmethyl-10-Hydroxycamptothecin Acetate Salt The title compound is prepared by the method of Example 8, by substituting bis(N-methylpiperazinyl)methane for bis(dimethylamino)methane.

EXAMPLE 11

Preparation of (20 S) 9-(4'-Piperidihopiperidinyl) Methyl-10-Hydroxycamptothecin Acetate Salt The title compound is prepared by the method of Example 8, by substituting bis(4'-piperidinopiperidinyl)methane for bis(dimethylamino)methane.

EXAMPLE 12

Preparation of (20 S) 9-Trimethylammoniummethyl-10-Hydroxycamptothecin Methanesulfonate Salt 65 mg of 9-N,N-dimethylaminomethyl-10-hydroxycamptothecin acetate salt, as prepared in Example 8, is dissolved in approximately 70 ml $CH_2Cl_2$ and filtered the filtrate is combined with methyl methanesulfonate (1 ml), cooled and partially concentrated under a stream of argon. After 4 hours, the solvent is concentrated to one-half volume and cooled. The precipitate is filtered, dissolved in water (10 ml), washed with ethyl acetate (3×10 ml) and then petroleum ether (10 ml), and lyophilized to give the title compounds.

EXAMPLE 13

Preparation of (20 S) 9-Cyclopropylaminomethyl-10-Hydroxycamptothecin Hydrochloride Salt 9-Cyclopropylaminomethyl-10-hydroxycamptothecin acetate salt is prepared according to the method of Example 8, by substituting bis(cyclopropylamino)methane for bis (dimethylamino)methane. The acetate salt is converted to the title hydrochloride salt by triturating with 0.1N HCl.

EXAMPLE 14

Preparation of/20 S) 9-Ethoxymethyl-10-Hydroxycamptothecin

The title compound is prepared by refluxing (20 S) 9-N,N-dimethylaminomethyl-10-hydroxycamptothecin hydrochloride salt as prepared in Example 7 with 95% ethanol.

EXAMPLE 15

Preparation of (20 S) 9-(N-Methylanilinomethyl)-10-Hydroxycamptothecin

The title compound is prepared according to the method of Example 8, wherein bis(N-methylanilino)methane is substituted for bis(dimethylamino)methane.

EXAMPLE 16

Preparation of (20 S) 9-Cyclohexylamino-methyl-10-Hydroxycamptothecin Hydrochloride Salt The title compound is prepared according to the method of Example 7, by substituting bis(cyclohexylamino)methane for bis(dimethylamino)methane.

EXAMPLE 17

Preparation of (20 S) 9-N,N-Dimethylaminoethylthiomethyl-10-Hydroxycamptothecin Hydrochloride Salt A mixture of (20 S) 9-N,N-dimethylaminomethyl-10-hydroxycamptothecin hydrochloride salt (100 mg) prepared as in Example 7, and 2-dimethylaminoethanethiol (13 ml) is heated at 85° C. under argon for five hours. The insoluble solid (excess thiol) is removed by filtration, and the filtrate is concentrated in vacuo to an oily residue which is purified using reversed phase MPLC. The product is eluted using 5% and 10% methanol in water to give the title compound as a yellow solid.

EXAMPLE 18

Preparation of (20 S) 9-N,N-Dimethylaminoethyloxymethyl-10-Hydroxycamptothecin Hydrochloride Salt A mixture of 9-N,N-dimethylaminomethyl-10-hydroxycamptothecin free base as prepared during the first reaction step of Example 7 (100 mg), in 2-dimethylaminoethanol (4 ml) containing three drops of 3N HCl is heated under argon at 80° C. for 24 hours. The semi-solid reaction mixture is treated with water (5 ml) and isopropanol (10 ml), stirred and filtered to give the title compound.

EXAMPLE 19

Preparation of (20 S) 9-N,N-Dimethylaminoethylaminomethyl-10-Hydroxycamptothecin Dihydrochloride Salt (20 S) 9-N,N-Dimethylaminoethylaminomethyl-10-hydroxycamptothecin acetate salt is prepared according to the method of Example 8, by substituting bis(dimethylaminoethyl-amino)methane for bis(dimethylamino)methane. The acetate salt obtained is treated with water (10 ml) and isopropanol (10 ml) containing 3N HCl (3 ml). The precipitated solid is collected, washed with isopropanol and dried to yield the title compound.

EXAMPLE 20

Preparation of (20 R,S) 9-N,N-Dimethylaminomethyl-10-Hydroxycamptothecin Acetate Salt The title compound is prepared as in Example 8, except that the starting material is racemic 10-hydroxycamptothecin prepared according to the method of Wani et al., J. Med. Chem., 23, 554 (1980). Racemic 10-hydroxycamptothecin can also be prepared from (20 S) 10-hydroxycamptothecin according to the following procedure:

(a) Preparation of 10-Hydroxy-20-chloro-20-deshydroxycamptothecin 7.8 g of 10-hydroxycamptothecin were suspended in 780 ml of methylene chloride at room temperature. 16 ml of pyridine were added, followed by 22 ml of thionyl chloride. The mixture was stirred under an atmosphere of nitrogen. The solid quickly dissolved to give a clear, bright-yellow solution which turned brown over about 15 hours. The solution was cooled to 0° C. and 780 ml of 4N aqueous hydrochloric acid were cautiously added to give a dark red slurry. After Warming to room temperature over about 2.5 hours the solid product was collected by filtration, washed with water and air dried to give 6.57 g of a yellow solid, m.p. 215-218 (dec). A second crop of 1.2 g was isolated by deposition from the reaction mother liquors.

(b) Preparation of 10-Hydroxy-20-deshydroxycamptothecin 6.03 g of product from the above reaction (a) were suspended with 5.15 g of activated zinc dust in 300 ml of glacial acetic acid. The resulting thick suspension was stirred vigorously at room temperature. After about 24 hours 6 ml of 4N aqueous hydrochloric acid were added, and stirring was continued for several hours. The yellow-orange slurry was diluted with 1200 ml of 1:1 (v/v) methanol:methylene chloride to give a clear brown solution with some suspended zinc particles. The solution was filtered through Celite and concentrated under vacuum to give a dark brown solid. The solid product was thoroughly washed with water, isolated by filtration and air dried to a constant weight of 5.36 g, m.p. 292° C. (dec).

(c) Preparation of (20 R,S) 10-Hydroxycamptothecin 2.51 g of product from the above procedure (b) were dissolved in 25 ml of N,N-dimethylformamide, and 1.6 ml of 40% aqueous dimethylamine were added to give a very dark solution. The mixture was stirred at ambient temperature as air was bubbled into the solution. After 5.5 hours the reaction was diluted with 75 ml of water to give a yellow-brown precipitate. The solid product was collected by filtration, washed with water and air dried to a constant weight of 1.97 g. This material was used to prepare the racemic title compound as described in Example 8.

EXAMPLE 21

Preparation of (20 S) 9-N,N-Dimethylaminomethyl-10-Hydroxycamptothecin Dihydrochloride Salt 9-N,N-Dimethylaminomethyl-10-hydrocamptothecin acetate salt (0.389 g) prepared as in Example 8 is dissolved in 0.4N hydrochloric acid (6 ml), lyophilized and pumped under high vacuum for 40 hours to yield the title compound.

EXAMPLE 22

Recrystallization of (20 S) 9-N,N-Dimethylaminomethyl-10-Hydroxycamptothecin Hydrochloride Salt 101 grams of the hydrochloride salt of the title compound (containing 84.0 g of free base) were dissolved by stirring at ambient temperature with 1000 ml of deionized water. The resulting thin slurry was filtered through a pad of Celite. An additional 500 ml. of water was used to wash the filter cake, and the clear liquors were combined. The liquors were concentrated by distillation at reduced pressure to approximately ½ volume. A thick, yellow slurry resulted. The slurry was gradually diluted with stirring by addition of 3000 ml of acetone. The pale yellow suspension was stirred at ambient temperature for a total of 16 hours. The solid product was collected by filtration and dried under vacuum to a constant weight. 86.8 g of product (91% yield corrected for free base content) m.p. 229°–230° C. were obtained.

EXAMPLE 23

Recrystallization of (20 S) 9-N,N-Dimethylaminomethyl-10-Hydroxycamptothecin Hydrochloride Salt 124 grams of the title compound (containing 90 grams of the free base) were stirred at ambient temperature with 1240 ml of deionized water. The resulting thin slurry was filtered through celite. After washing the filter cake with water, the combined aqueous layers were concentrated to ½ volume and then diluted with 1860 ml (15 volumes v/w) of 1-propanol. The solution was concentrated by vacuum distillation while azeotroping with an additional 3720 ml (30 volumes v/w) of 1-propanol added in portions. Distillation was continued to a final volume of approximately 1860 ml (15 volumes v/w). The suspension was stirred at ambient temperature for several hours to complete crystallization. The solid product was collected and dried to a constant weight. The product obtained weighed 113 g (92% recovery, corrected for the free base content) m.p. 229°–230° C.

What we claim is:

1. A method for preparing a first compound selected from the group consisting of:

(20S) 9-N,N-dimethylaminomethyl-10-hydroxycamptothecin;

(20S) 9-morpholinomethyl-10-hydroxycamptothecin;

(20S) 9-N-methylpiperazinylmethyl-10-hydroxycamptothecin;

(20S) 9-(4'-piperidinopiperidinyl)methyl-10-hydroxycamptothecin;

(20S) 9-cyclopropylaminomethyl-10-hydroxycamptothecin;

(20S) 9-(methylanilinomethyl)-10-hydroxycamptothecin; and (20S) 9-cyclohexylaminomethyl-10-hydroxycamptothecin; comprising the steps of:

a) hydrogenating camptothecin of greater than 96% purity to provide 1,2,6,7-tetrahydrocamptothecin, further comprising the steps of:

1) mixing camptothecin; a first solvent of acetic acid; a hydrogenation catalyst selected from the group consisting of: platinum, platinum dioxide, 5% platinum-on-carbon, 5% platinum-on-sulfided carbon, and 5% platinum-on-alumina; and a hydrogenation catalyst moderator selected from the group consisting of: dimethyl sulfoxide and thiophene, with the proviso that no hydrogenation catalyst moderator is used when the hydrogenation catalyst is 5% platinum-on-sulfided carbon; in a reaction vessel to form a first reaction mixture; said first solvent being present in a v/w ratio of about 10–30 volumes first solvent per weight of camptothecin; said hydrogenation catalyst moderator being present in a v/v ratio of about 0.2–5 vol. % moderator to first solvent volume;

2) charging said reaction vessel with hydrogen to atmospheric or higher pressure; and 3) heating said first reaction mixture at a temperature of about ambient to about 90° C. to provide 1,2,6,7-tetrahydrocamptothecin;

b) oxidizing said 1,2,6,7-tetrahydrocamptothecin to 10-hydroxycamptothecin, further comprising the steps of:

1) preparing a solution of said 1,2,6,7-tetrahydrocamptothecin in a second solvent selected from the group consisting of: acetic acid, acetone, N,N-dimethylformamide, and a low molecular weight alcohol selected from the group consisting of: methanol, ethanol, and i-propanol; and water to provide a second reaction mixture wherein the water: second solvent v/v ratio is about 25–75% water by volume; and 2) addition of from greater than about 2 to about 3 eq. of an oxidizing agent selected from a group consisting of: potassium permanganate, sodium periodate, potassium periodate, iodosobenzene, and esters of iodosobenzene selected from a group consisting of: iodobenzene(bis)trifluoroacetate, iodobenzenediacetate, and hydroxy(tosyloxy)iodobenzene; to said second reaction mixture to provide said 10-hydroxycamptothecin; and c) preparing said first compound by Mannich reaction, further comprising the steps of:

1) making a slurry of said 10-hydroxycamptothecin in a third solvent selected from the group consisting of: acetic acid, acetonitrile, and inert chlorinated hydrocarbon, low molecular weight alcohol, and mixtures thereof; to provide a third reaction mixture; and 2) adding a molar excess of a second compound selected from the group consisting of:
bis(dimethylamino)methane;
bis(N-morpholino)methane;
bis(N-methylpiperazinyl)methane;
bis(4'-piperidinopiperidinyl)methane;
bis(cyclopropylamino)methane;
bis(N-methylanilino)methane; and
bis(cyclohexylamino)methane
to said third reaction mixture at a temperature from 0° C. to the reflux temperature of said third solvent to provide said first compound.

2. A method of claim 1 wherein said compound is 9-N,N-dimethylaminomethyl-10-hydroxycamptothecin.

3. A method of claim 1 further comprising the step, said step preceding step a), of purifying camptothecin extracted from *Camptotheca accuminata* or *Nothapodytes foetida* of less than about 96% purity to greater than 96% purity, comprising recrystallizing said camptothecin from 10–35 volumes v/w of a recrystallization solvent selected from the group consisting of: N,N-dimethylformamide, N-methylpyrrolidone, acetic acid, trifluoroacetic acid, dimethylsulfoxide, a mixture of acetic acid and dimethylsulfoxide, a mixture of ethanol and dimethylsulfoxide, and a mixture of acetic acid and hydrochloric acid heated to temperature from about 60° C. to reflux.

4. A method of claim 3 wherein said crude camptothecin is extracted from *Nothapodytes foetida* and is recrystallized from acetic acid and then N,N-dimethylformamide.

5. A method of claim 4 further comprising the steps of:

a) dissolving said crude camptothecin in acetic acid to form a first camptothecin solution;

b) adding about 10% by weight activated charcoal to said first camptothecin solution;

c) precipitating a first precipitate;

d) stirring said first precipitate in N,N-dimethylformamide at about 100° C. for up to 24 h; and e) collecting purified camptothecin.

6. A method of claim 3 wherein said crude camptothecin is extracted from *Camptotheca accuminata* and is recrystallized from N,N-dimethylformamide.

7. A method of claim 6 further comprising the steps of:

a) stirring said crude camptothecin in N,N-dimethylformamide at about 100° C. for up to 24 h;

b) cooling to ambient temperature and collecting purified camptothecin; and c) optionally repeating steps a) and b) to further purify said camptothecin.

8. A method according to claim 1 wherein said hydrogenation catalyst is 5% platinum-on-carbon.

9. A method according to claim 8 wherein said hydrogenation catalyst is present in 20–110% w/w relative to camptothecin weight.

10. A method according to claim 9 wherein said hydrogenation catalyst is present in about 2.5% Pt w/w relative to camptothecin weight.

11. A method according to claim 1 wherein said hydrogenation catalyst moderator is dimethylsulfoxide.

12. A method according to claim 1 wherein said hydrogen pressure is about 50–70 psi.

13. A method according to claim 1 wherein said first solvent is present in a v/w ratio of about 10 volumes first solvent per weight of camptothecin.

14. A method according to claim 1 wherein said first reaction mixture is heated at a temperature of about 40°–80° C.

15. A method according to claim 1 wherein said second solvent is acetic acid.

16. A method according to claim 1 wherein said water: second solvent v/v ratio is about 50% water by volume.

17. A method according to claim 1 wherein said oxidizing agent is iodobenzenediacetate.

18. A method according to claim 1 wherein said third solvent is a mixture of an inert chlorinated hydrocarbon and a low molecular weight alcohol.

19. A method according to claim 18 wherein said inert chlorinated hydrocarbon is methylene chloride.

20. A method according to claim 18 wherein said low molecular weight alcohol is 1-propanol.

21. A method according to claim 18 wherein said low molecular weight alcohol is methanol.

22. A method according to claim 18 wherein the v/v ratio of inert chlorinated hydrocarbon: low molecular weight alcohol is about 2:1.

23. A method according to claim 1 for preparing monohydrochloride salts of said compounds, further comprising the step of:
 c) 3) addition of a molar excess of hydrochloric acid.

24. A method for preparing 9-N,N-dimethylaminomethyl-10-hydroxycamptothecin comprising the steps of:
 a) hydrogenating camptothecin of greater than 96% purity to provide 1,2,6,7-tetrahydrocamptothecin, further comprising the steps of:
  1) mixing camptothecin; a first solvent consisting of acetic acid, a hydrogenation catalyst consisting of 5% platinum-on-carbon, and a hydrogenation catalyst moderator consisting of dimethylsulfoxide in a reaction vessel to form a first reaction mixture; said first solvent being present in a v/w ratio of about 10 volumes first solvent per weight of camptothecin; said hydrogenation catalyst being present in about 2.5% Pt w/w relative to camptothecin weight; said hydrogenation catalyst moderator being preset in a v/v ratio of about 0.2–5 vol. % moderator to first solvent volume;
  2) charging said reaction vessel with hydrogen to 50–70 psi; and
  3) heating said first reaction mixture at a temperature of about 40°–80° C. to provide 1,2,6,7-tetrahydrocamptothecin;
 b) oxidizing said 1,2,6,7-tetrahydrocamptothecin to 10-hydroxycamptothecin, further comprising the steps of:
  1) preparing a solution of said 1,2,6,7-tetrahydrocamptothecin in a second solvent consisting of a mixture of acetic acid and water to provide a second reaction mixture wherein the water: second solvent v/v ratio is about 50% water by volume; and
  2) adding about 3 eq. of iodobenzenediacetate to said second reaction mixture to provide said 10-Hydroxycamptothecin; and
 c) preparing 9-N,N-dimethylaminomethyl-10-hydroxycamptothecin hydrochloride by Mannich reaction, further comprising the steps of:
  1) adding said 10-hydroxycamptothecin to a third solvent consisting of a mixture of methylene chloride and 1-propanol to provide a third reaction mixture wherein the v/v ratio of methylene chloride: 1-propanol is about 2:1;
  2) addition of a molar excess of bis(dimethylamino)methane to said third reaction mixture at ambient temperature.

25. A method according to claim 24 for preparing 9-N,N-dimethyl-aminomethyl-10-hydroxycamptothecin hydrochloride, further comprising the step of:
 c) 3) addition of a molar excess of hydrochloric acid to provide 9-N,N-dimethyl-aminomethyl-10-hydroxycamptothecin hydrochloride.

26. A method of claim 24 further comprising the step, said step preceding step a), of purifying camptothecin of less than about 96% purity to greater than 96% purity comprising recrystallizing said camptothecin 10–35 volumes v/w of a recrystallization solvent selected from the group consisting of: N,N-dimethylformamide, N-methylpyrrolidone, acetic acid, trifluoroacetic acid, dimethylsulfoxide, a mixture of acetic acid and dimethylsulfoxide, a mixture of ethanol and dimethylsulfoxide, and a mixture of acetic acid and hydrochloric acid heated to a temperature from about 60° C. to reflux.

27. A method of claim 26 wherein said crude camptothecin is extracted from *Nothapodytes foetida* and is recrystallized from acetic acid and then N,N-dimethylformamide.

28. A method of claim 27 further comprising the steps of:
 a) dissolving said camptothecin starting material in acetic acid to form a first camptothecin solution;
 b) adding about 10% by weight activated charcoal to said first camptothecin solution;
 c) precipitating a first precipitate;
 d) stirring said first precipitate in N,N-dimethylformamide at about 100° C. for up to 24 h; and
 e) collecting purified camptothecin.

29. A method of claim 26 wherein said crude camptothecin is extracted from *Camptotheca accuminata* and is recrystallized from N,N-dimethylformamide.

30. A method of claim 29 further comprising the steps of:
 a) stirring said camptothecin starting material in N,N-dimethylformamide at about 100° C. for up to 24 h;
 b) cooling to ambient temperature and collecting purified camptothecin; and
 c) optionally repeating steps a) and b) to further purify said camptothecin.

31. A method of preparing 1,2,6,7-tetrahydrocamptothecin comprising the steps of:
 1) mixing camptothecin of greater than 96% purity; acetic acid; a hydrogenation catalyst selected from the group consisting of: platinum, platinum dioxide, 5% platinum-on-carbon, 5% platinum-on-sulfided carbon, and 5% platinum-on-alumina; and a hydrogenation catalyst moderator selected from the group consisting of: dimethyl sulfoxide and thiophene, with the proviso that no hydrogenation catalyst moderator is used when the hydrogenation catalyst is 5% platinum-on-sulfided carbon; in a reaction vessel to form a reaction mixture; said acetic acid being present in a v/w ratio of about 10–30 volumes per weight of camptothecin; said hydrogenation catalyst moderator being present in a v/v ratio of about 0.2–5 vol. % moderator to acetic acid volume;
 2) charging said reaction vessel with hydrogen to atmospheric or higher pressure; and 3) heating said reaction mixture at a temperature of about ambient to about 90° C. to provide 1,2,6,7-tetrahydrocamptothecin.

32. A method according to claim 31 wherein said hydrogenation catalyst is 5% platinum-on-carbon.

33. A method according to claim 32 wherein said hydrogenation catalyst is present in 20–110% w/w relative to camptothecin weight.

34. A method according to claim 33 wherein said hydrogenation catalyst is present in about 2.5% Pt w/w relative to camptothecin weight.

35. A method according to claim 31 wherein said hydrogenation catalyst moderator is dimethylsulfoxide.

36. A method according to claim 31 wherein said hydrogen pressure is about 50–70 psi.

37. A method according to claim 31 wherein said acetic acid is present in a v/w ratio of about 10 volumes per weight of camptothecin.

38. A method according to claim 31 wherein said reaction mixture is heated at a temperature of about 40°–80° C.

39. A method according to claim 4 wherein, in said step preceding step a), said camptothecin is initially of less than about 98% purity and is purified to at least about 98% purity.

40. A method according to claim 6 wherein, in said step preceding step a), said camptothecin is initially of less than about 98% purity and is purified to at least about 98% purity.

41. A method according to claim 27 wherein, in said step preceding step a), said camptothecin is initially of less than about 98% purity and is purified to at least about 98% purity.

42. A method according to claim 29 wherein, in said step preceding step a), said camptothecin is initially of less than about 98% purity and is purified to at least about 98% purity.

* * * * *